US010101305B2

(12) United States Patent
Ohashi

(10) Patent No.: US 10,101,305 B2
(45) Date of Patent: Oct. 16, 2018

(54) CHROMATOGRAPH DATA PROCESSING SYSTEM AND DATA PROCESSING METHOD

(71) Applicant: Shimadzu Corporation, Kyoto-shi, Kyoto (JP)

(72) Inventor: Hiroshi Ohashi, Otsu (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 307 days.

(21) Appl. No.: 14/636,443

(22) Filed: Mar. 3, 2015

(65) Prior Publication Data

US 2015/0253293 A1    Sep. 10, 2015

(30) Foreign Application Priority Data

Mar. 4, 2014  (JP) ................................ 2014-041743

(51) Int. Cl.
*G01N 31/00*  (2006.01)
*G01N 30/02*  (2006.01)
(Continued)

(52) U.S. Cl.
CPC ......... *G01N 30/02* (2013.01); *G01N 30/8658* (2013.01); *G01N 2030/027* (2013.01); *G01N 2030/8804* (2013.01)

(58) Field of Classification Search
CPC ...... C08L 83/08; C08L 83/00; C08L 2666/28; C08L 2666/44; C08L 2666/54;
(Continued)

(56) References Cited

U.S. PATENT DOCUMENTS

2013/0018598 A1 *  1/2013  Ohashi ................... G01N 30/34
                                                      702/25

FOREIGN PATENT DOCUMENTS

CN        102394977 A      3/2012
JP        2013-024603 A    2/2013
JP        WO2013/011818 A1 2/2015

OTHER PUBLICATIONS

Office Action dated Mar. 3, 2016, issued in counterpart Chinese Patent Application No. 201510094362.6, with English translation. (25 pages).

* cited by examiner

*Primary Examiner* — Robert Bachner
(74) *Attorney, Agent, or Firm* — Westerman, Hattori, Daniels & Adrian, LLP

(57) ABSTRACT

Provided is a chromatograph data processing system for presenting unexamined analysis conditions to a user in an easily understood manner when changing a plurality of analysis condition parameters. The system is used for a chromatograph for analyzing a sample according to a schedule table in which a plurality of analysis conditions and execution order of a plurality of analyses are described, each of the plurality of analysis conditions being defined by a combination of control parameter values. The system includes: memory 61 for storing a plurality of analysis conditions; unexamined analysis condition creator 66 for creating all combinations of values of control parameters included in the plurality of analysis conditions, and for creating a list of unexamined analysis conditions from the created combinations, the list being composed of analysis conditions that are not included in the plurality of analysis conditions stored in the memory 61; and display section 72.

4 Claims, 3 Drawing Sheets

(51) Int. Cl.
    *G01N 30/86*     (2006.01)
    *G01N 30/88*     (2006.01)
(58) Field of Classification Search
    CPC ........... D06M 15/6436; D06M 15/643; D06M 15/65; D06M 15/647; D06M 11/79; D06M 13/513; D06M 15/6433; D06M 11/50; D06M 13/11
    See application file for complete search history.

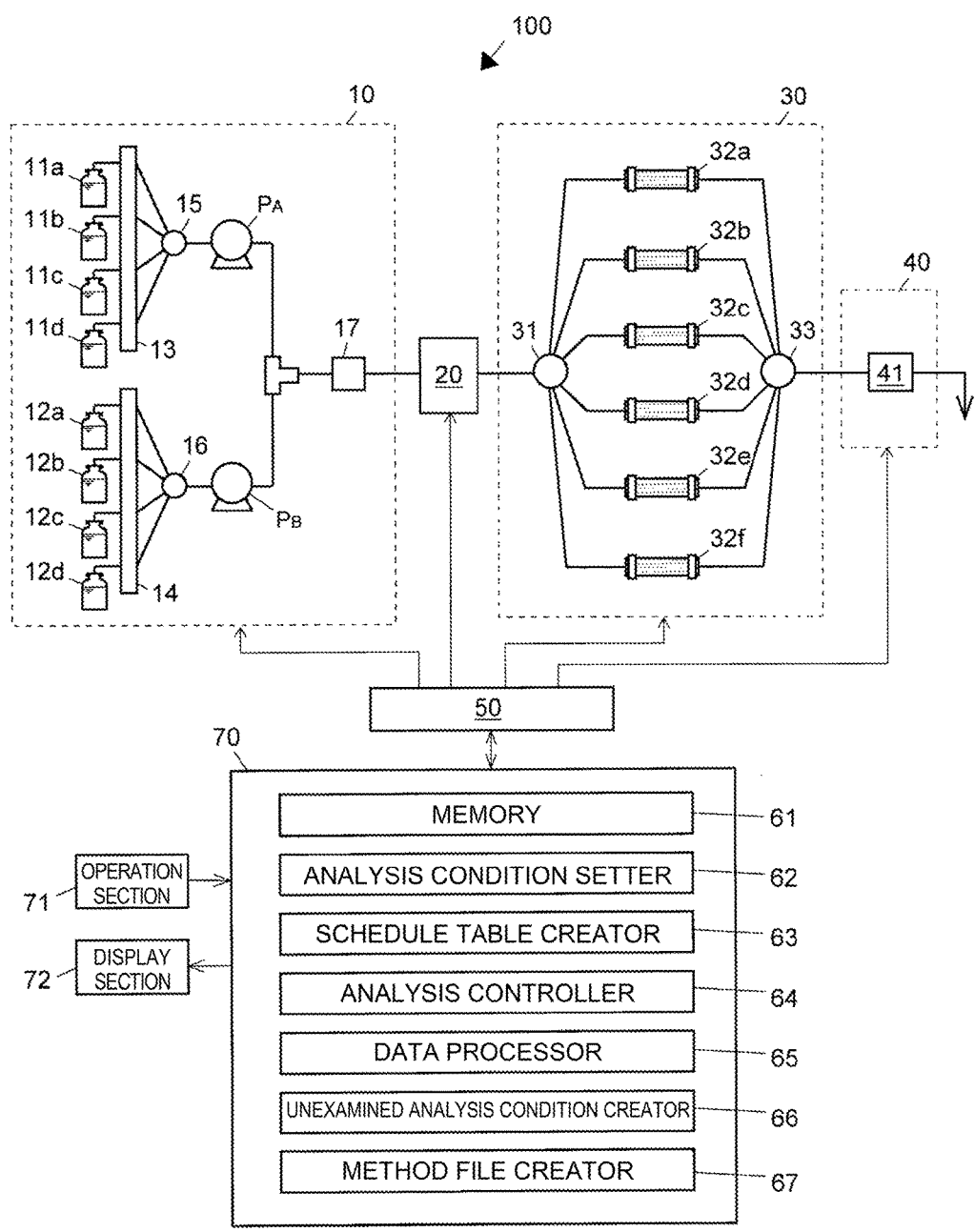

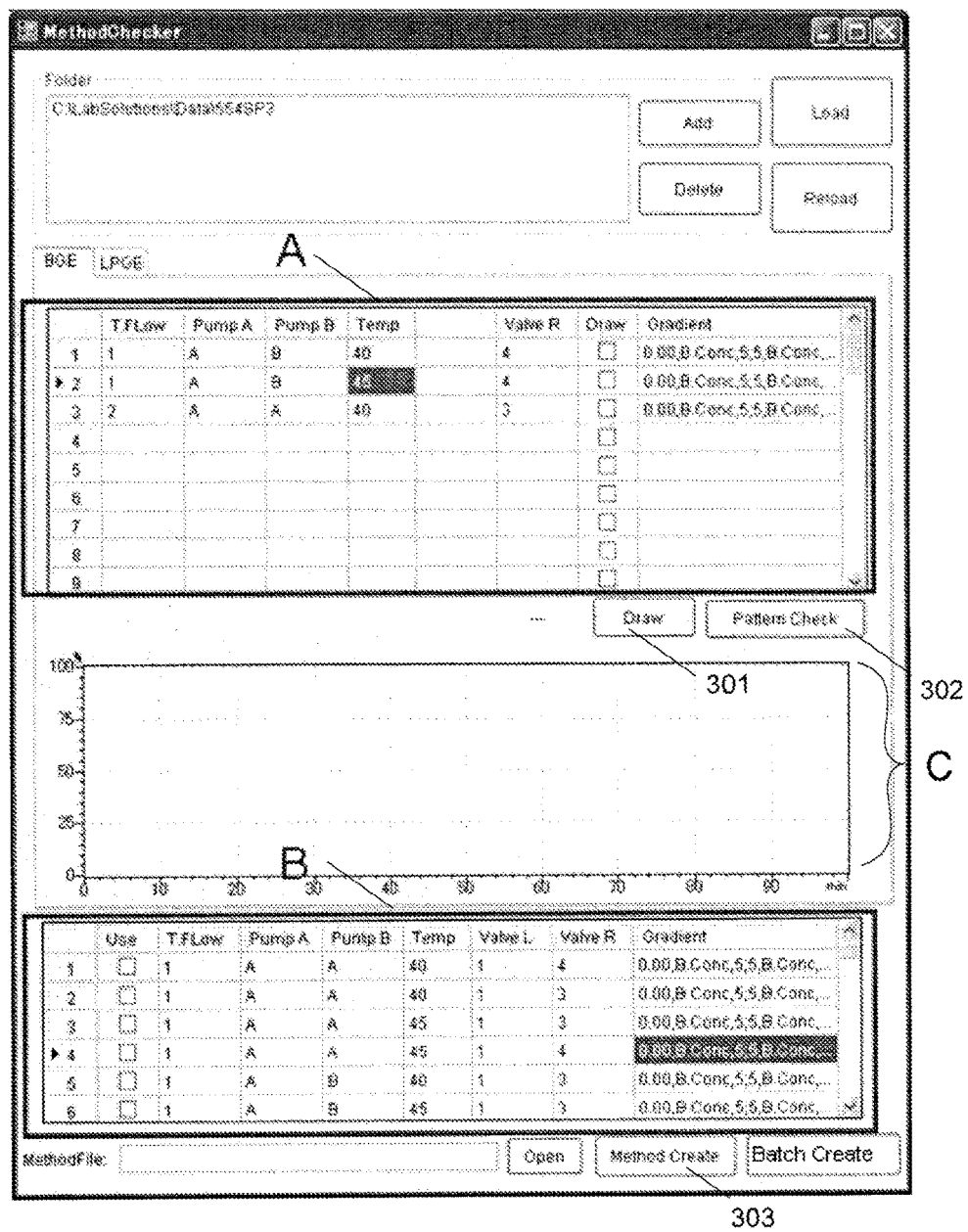

CHROMATOGRAPH DATA PROCESSING SYSTEM AND DATA PROCESSING METHOD

TECHNICAL FIELD

The present invention relates to a chromatograph data processing system, and data processing method.

BACKGROUND ART

A liquid chromatograph is an analysis apparatus in which: a mobile phase (also called eluent) of a liquid and a sample injected into the mobile phase are pressurized by a pump or the like to be caused to pass through a column; and components in the sample are separated and detected based on a difference in interaction (such as adsorption, distribution, ion exchange, and size exclusion) between a stationary phase (also called filler) and the mobile phase in the column.

In the liquid chromatograph, a sample is analyzed under various conditions, in some cases, in order to find the best analysis conditions for the sample (hereinafter, this operation is called method scouting). In the method scouting, the kind of mobile phase, the kind of column, the flow rate of a pump, the temperature of a column oven for heating the column, and the like are set as parameters. Hence, the liquid chromatograph that performs the method scouting is capable of switching these parameters (see Patent Literature 1).

An example of the liquid chromatograph as described above is illustrated in FIG. 4. A liquid chromatograph 1 of FIG. 4 includes a liquid-sending section 10, an auto-sampler 20, a column oven 30, a detection section 40, a system controller 50 for controlling each of these sections, and a control system 60 for managing analysis operations through the system controller 50 and processing data obtained by the detection section 40. An operation section 71 including a keyboard and a mouse, and a display section 72 including a display unit are connected to the control system 60. A plurality of columns 32a to 32f are provided in the column oven 30, and the plurality of columns 32a to 32f are switched by passage-switching sections 31 and 33. In the liquid-sending section 10, solvent containers 11a to 11d and 12a to 12d in which various mobile phases are contained are respectively connected to liquid-sending pumps $P_A$ and $P_B$ through deaerators 13 and 14 and solvent-switching valves 15 and 16. Examples of the used mobile phases include: aqueous solvents such as water and aqueous solutions obtained by adding various salts to water; and organic solvents such as methanol, acetonitrile and hexane. An aqueous solvent drawn from one of the solvent containers 11a to 11d and an organic solvent drawn from one of the solvent containers 12a to 12d are mixed with each other by a gradient mixer 17 as needed, whereby a mobile phase having a predetermined composition is prepared.

The mobile phase having the predetermined composition that is prepared by the liquid-sending section 10 passes through the auto-sampler 20 to flow into one of the plurality of columns 32a to 32f in the column oven 30. Before that, a sample is injected into the mobile phase by the auto-sampler 20, and the sample passes through the column while being carried by the flow of the mobile phase. In the process, components in the sample are temporally separated and sequentially detected by the detection section 40 provided with a detector 41 such as a photodiode array (PDA) detector.

A number of analyses under various analysis conditions are controlled by the control system 60 embodied by a computer, and are automatically processed. The various analysis conditions are described in a file called "method file", which is managed by an analysis condition setter 62 in the control system 60, and is stored in a memory 61 in the control system 60. Here, an analysis condition means a combination of parameters (such as the kind of mobile phase, the kind of column, the flow rate of a pump, and the temperature of a column oven that are used in analysis) for controlling operations of the sections constituting the chromatograph. A schedule table creator 63 in the control system 60 creates a file of data called a "schedule table" which is a table describing which analysis conditions are executed in which order. In the schedule table, a sample to be analyzed and an analysis condition for the sample are described in a row, and a series of rows are listed in the columnar direction as analysis time series. A method file is cited as the analysis condition. According to the schedule table, an analysis controller 64 in the control system 60 controls each section in the liquid chromatograph 1 such that a series of analyses are executed under the analysis conditions at predetermined timing. A data processor 65 in the control system 60 acquires an analysis result under each analysis condition and performs processes such as chromatogram creation.

CITATION LIST

Patent Literature

[Patent Literature 1] JP 2013-024603 A

SUMMARY OF INVENTION

Technical Problem

The method scouting includes: describing some analysis conditions to be examined in a schedule table; acquiring analysis results; and then making other analysis conditions to be further examined, in consideration of control parameters used in the analysis and the analysis results. Along with an increase in performance of the control system 60, in recent years, the number of analysis conditions examined in the method scouting tends to increase, and the number of settable control parameters is large. Hence, in the stage in which analysis results are acquired for some analysis conditions, it may become difficult for a user to understand which analysis conditions are unexamined.

The present invention, which has been made in view of the above, has an object to provide a chromatograph data processing system capable of presenting unexamined analysis conditions to a user in an easily understood manner when the user examines and changes a plurality of parameters in analysis conditions.

Solution to Problem

A chromatograph data processing system according to the present invention, which has been made in order to achieve the above-mentioned object, is a chromatograph data processing system used for a chromatograph for analyzing a sample according to a schedule table in which a plurality of analysis conditions and execution order of a plurality of analyses are described, each of the plurality of analysis conditions being defined by a combination of values of a plurality of control parameters, the data processing system including: a) a memory for storing a plurality of analysis conditions under which analyses have been executed for a sample; b) an unexamined analysis condition creator for creating all combinations of values of control parameters included in the plurality of analysis conditions, and for creating a list of unexamined analysis conditions from the created combinations, the list being composed of analysis conditions that are not included in the plurality of analysis conditions stored in the memory; and c) a display section for displaying the list.

Moreover, a chromatograph data processing method according to the present invention, which has been made in order to achieve the above-mentioned object, is a chromatograph data processing method used for a chromatograph for analyzing a sample according to a schedule table in which a plurality of analysis conditions and execution order of a plurality of analyses are described, each of the plurality of analysis conditions being defined by a combination of values of a plurality of control parameters, the data processing method including the steps of: a) storing a plurality of analysis conditions under which analyses have been executed for a sample; b) creating all combinations of values of control parameters included in the plurality of analysis conditions and creating a list of unexamined analysis conditions from the created combinations, the list being composed of analysis conditions that are not included in the plurality of analysis conditions; and c) displaying the list.

The chromatograph data processing system may have a configuration that the unexamined analysis condition creator further acquire chromatograms respectively obtained for the plurality of analysis conditions under which the analyses have been executed, and the chromatograph data processing system may display one or more of the chromatograms on the display section, in the case where a user gives an instruction to that effect.

The chromatograph data processing system may further include a method file creator for creating one or more of method files corresponding to one or more of the analysis conditions included in the list, in the case where a user gives an instruction to that effect.

Advantageous Effects of Invention

In the chromatograph data processing system and the chromatograph data processing method configured as described above according to the present invention, in the case where method scouting is performed for a plurality of analysis conditions, unexamined analysis conditions are displayed as a list in an easily understood manner for a user, and hence the user can easily make other analysis conditions to be further examined.

BRIEF DESCRIPTION OF DRAWINGS

FIG. 1 is a diagram describing a liquid chromatograph including a chromatograph data processing system according to an embodiment of the present invention.

FIG. 2 is a diagram describing a display screen of the liquid chromatograph according to the embodiment.

FIG. 3 is a diagram illustrating an example of a schedule table used in the embodiment.

DESCRIPTION OF EMBODIMENTS

Figure 4:
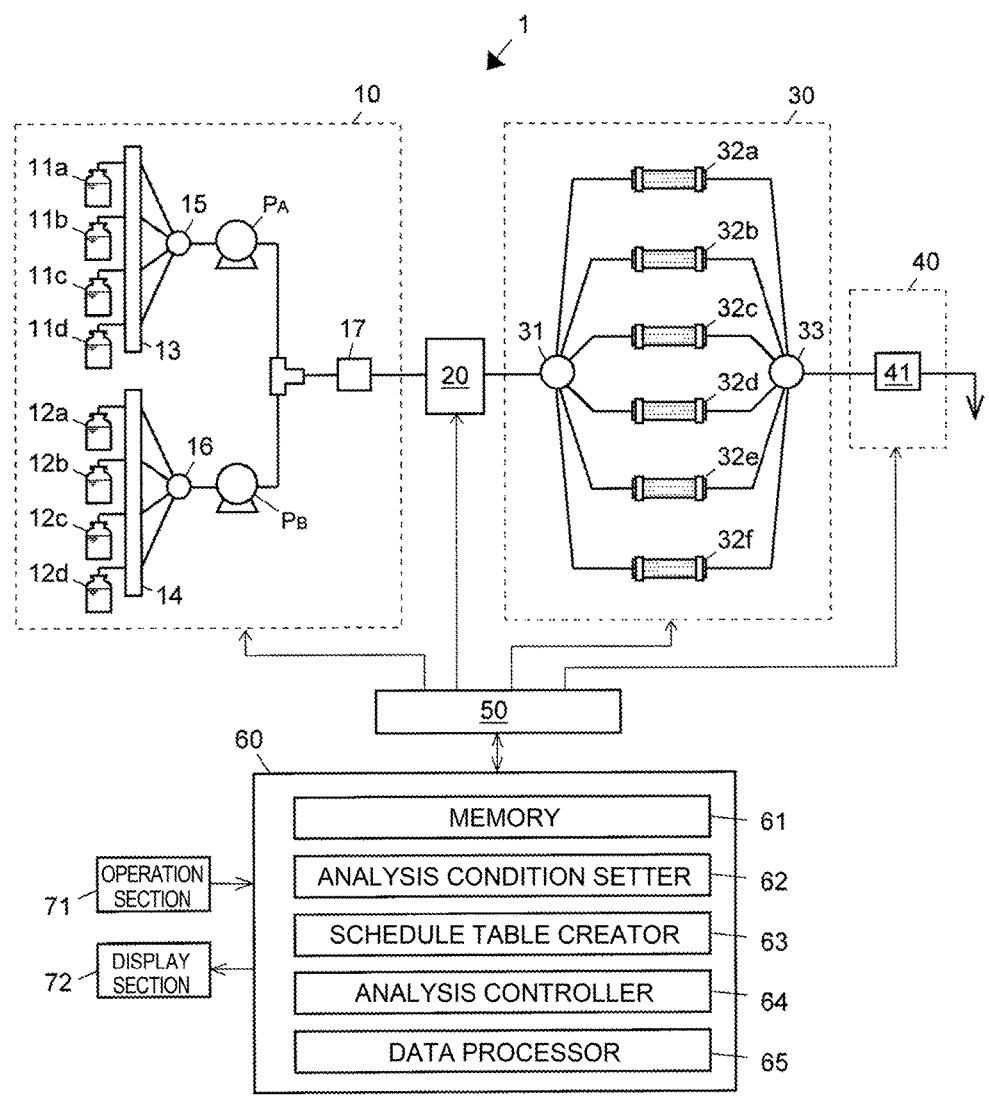
FIG. 4 is a diagram describing a conventional liquid chromatograph.

Hereinafter, modes for carrying out the present invention are described by way of embodiments.

FIG. 1 is a schematic configuration diagram of a liquid chromatograph including a chromatograph data processing system according to an embodiment of the present invention. The same constituent elements as those in FIG. 4 are denoted by the same reference signs, and description thereof is omitted as appropriate.

A liquid chromatograph 100 of the present embodiment includes a liquid-sending section 10, an auto-sampler 20, a column oven 30, a detection section 40, a system controller 50, and a control system 70. An operation section 71 including a keyboard and a mouse and a display section 72 including a display unit are connected to the control system 70. The control system 70 corresponds to a chromatograph data processing system of the present invention. The control system 70 includes a memory 61, an analysis condition setter 62, a schedule table creator 63, an analysis controller 64, and a data processor 65, similarly to the control system 60 of the conventional liquid chromatograph 1. In addition, the control system 70 includes an unexamined analysis condition creator 66 and a method file creator 67, and is embodied by a computer.

The liquid chromatograph according to the present embodiment has characteristics in operations at the time of condition setting in performing method scouting, and the control system 70 assists a user in condition setting in the following manner. It is assumed here that one kind of sample is a target of the method scouting, for ease of description. Moreover, description is given of the stage in which: all analyses according to a schedule table illustrated in FIG. 3 are executed; and other analysis conditions are further examined in consideration of the analysis results.

"File 1", "File 2", and "File 3" are respectively cited in rows of analysis Nos. 1 to 3 in the schedule table in FIG. 3. "File 1", "File 2", and "File 3" are method files in which analysis conditions are described, and one or more values of control parameters (such as the flow rate of a mobile phase, the kind of mobile phase, the temperature of a column oven, and the kind of column that are used in analysis) for controlling operations of the sections constituting the chromatograph are different among the described analysis conditions. In all of "File 1", "File 2", and "File 3", one kind of sample ("Sample 1") is defined as a target.

It the stage in which all the analyses according to the schedule table illustrated in FIG. 3 are executed, the memory 61 in the control system 70 stores: the method files (Files 1 to 3) for the analyses that have already been executed; and chromatograms that are created by the data processor 65 as results of the analyses according to the method files.

If the user operates the operation section 71 to instruct the control system 70 to examine analysis conditions other than the analysis conditions described in the method files "File 1" to "File 3", the unexamined analysis condition creator 66 in the control system 70 reads out "File 1" to "File 3" from the memory 61, and extracts control parameters described in each method file. Then, the unexamined analysis condition creator 66 creates an analysis history list including the extracted control parameters as listed items, for the analysis conditions described in "File 1" to "File 3".

For example, it is assumed that the analysis condition described in each method file is as follows.

"File 1": the flow rate of the mobile phase: 1 mL, the kind of mobile phase: α, the temperature of the column oven: 40° C., the used column: 4

"File 2": the flow rate of the mobile phase: 1 mL, the kind of mobile phase: α, the temperature of the column oven: 45° C., the used column: 4

"File 3": the flow rate of the mobile phase: 2 mL, the kind of mobile phase: β, the temperature of the column oven: 40° C., the used column: 3

Four values of "the flow rate of the mobile phase", "the kind of mobile phase", "the temperature of the column oven", and "the kind of used column" are different among the analysis conditions described in these method files, and hence the unexamined analysis condition creator 66 extracts the four control parameters. The unexamined analysis condition creator 66 creates an analysis history list including the four extracted control parameters as listed items, for the analysis conditions described in these method files, and the control system 70 displays the analysis history list on a screen of the display section 72 as illustrated in, for example, A in FIG. 2. Columns indicated by "Pump A" and "Pump B" in the analysis history list in FIG. 2 respectively show the kinds of solvent drawn by liquid-sending pumps $P_A$ and $P_B$. Moreover, "A" in the column of "Pump A" means the solvent in the solvent container 11a, "A" in the column of "Pump B" means the solvent in the solvent container 12a, and "B" in the column of "Pump B" means the solvent in the solvent container 12b. The kind of mobile phase α means a mobile phase obtained by mixing the solvent in the solvent container 11a drawn by the liquid-sending pump $P_A$ with the solvent in the solvent container 12a drawn by the liquid-sending pump $P_B$, and the kind of mobile phase 3 means a mobile phase obtained by mixing the solvent in the solvent container 11a drawn by the liquid-sending pump $P_A$ with the solvent in the solvent container 12b drawn by the liquid-sending pump $P_B$.

After that, if the user operates the operation section 71 to click an operation button 302 displayed as "Pattern Check" in FIG. 2, the unexamined analysis condition creator 66 creates all combinations of values of the control parameters extracted in the above, and extracts, as unexamined analysis conditions, combinations other than the same combinations as those described in "File 1" to "File 3", from the created combinations. Then, the unexamined analysis condition creator 66 creates an unexamined analysis condition list including the control parameters as listed items, for the unexamined analysis conditions.

In the example described above, the values of the four extracted control parameters have two patterns (1 mL and 2 mL) for the flow rate of the mobile phase, two patterns (α and β) for the kind of mobile phase, two patterns (40° C. and 45° C.) for the temperature of the column oven, and two patterns (3 and 4) for the used column, and hence the unexamined analysis condition creator 66 creates combinations of sixteen patterns (=2×2×2×2) as all the combinations of the values of the control parameters. Further, the unexamined analysis condition creator 66 excludes combinations of three patterns described in the method files (Files 1 to 3) for the analyses that have already been executed, from the combinations of sixteen patterns, and extracts the resultant combinations of thirteen patterns as unexamined analysis conditions. Then, the unexamined analysis condition creator 66 creates an unexamined analysis condition list including "the flow rate of the mobile phase", "the kind of mobile phase", "the temperature of the column oven", and "the kind of used column" as listed items, for the thirteen patterns of the unexamined analysis conditions, and the control system 70 displays the unexamined analysis condition list on the screen of the display section 72 as illustrated in, for example, B in FIG. 2.

As described above, according to the control system 70 of the present embodiment, unexamined analysis conditions are displayed as a list in an easily understood manner for the user. This enables the user to easily determine other analysis conditions to be further examined in method scouting.

Further, if the user operates the operation section 71 to check one or more of checkboxes provided in the analysis history list (A in FIG. 2) displayed on the display section 72 and then click an operation button 301 displayed as "Draw" in FIG. 2, the unexamined analysis condition creator 66 acquires, from the memory 61, one or more of chromatograms obtained for one or more of analyses corresponding to one or more of checked rows, and the control system 70 displays the one or more of chromatograms on the display section 72 (a region C in FIG. 2) along with the analysis history list.

Because the control system 70 including the unexamined analysis condition creator 66 has these functions, the user can check control parameters that have already been used in analysis, through the analysis history list, and can check an analysis result corresponding to a designated analysis condition, through the chromatogram. Hence, the user can easily obtain information that helps to make other analysis conditions to be further examined in method scouting.

Further, if the user operates the operation section 71 to check one or more of checkboxes provided in the unexamined analysis condition list (B in FIG. 2) displayed on the display section 72 and then click an operation button 303 displayed as "Method Create" in FIG. 2, the method file creator 67 creates one or more of method files corresponding to one or more of checked rows. This can facilitate preparation for executing other analysis conditions to be further examined. Such an additional function is not essential, and hence the method file creator 67 in the control system 70 is not an essential constituent element.

Although the embodiment and the conventional example are described above using the liquid chromatographs, solutions provided by the present invention do not depend on the state of a mobile phase (for example, whether the mobile phase is a liquid phase or a gas phase), and hence it is obvious that a data processing system and a data processing method according to the present invention can also be applied to other chromatographs such as a gas chromatograph.

REFERENCE SIGNS LIST 1, 100 . . . Liquid Chromatograph
10 . . . Liquid-Sending Section
11a to 11d, 12a to 12d . . . Solvent Container
13, 14 . . . Deaerator
15, 16 . . . Solvent-Switching Valve
17 . . . Gradient Mixer
20 . . . Auto-Sampler
30 . . . Column Oven
31, 33 . . . Passage-Switching Section
32a to 32f . . . Column
40 . . . Detection Section
41 . . . Detector
50 . . . System Controller
60, 70 . . . Control System
61 . . . Memory
62 . . . Analysis Condition Setter
63 . . . Schedule Table Creator
64 . . . Analysis Controller
65 . . . Data Processor
66 . . . Unexamined Analysis Condition Creator
67 . . . Method File Creator
71 . . . Operation Section
72 . . . Display Section
301, 302, 303 . . . Operation button

The invention claimed is:

1. A chromatograph data processing system used for a chromatograph comprising:
   a) a memory configured to store a plurality of analysis conditions under which analyses have been executed for a sample, the plurality of analysis conditions being described in a schedule table, each of the plurality of analysis conditions being defined by a combination of values of control parameters;
   b) an unexamined analysis condition creator configured to create all combinations of the values of the control parameters included in all of the plurality of analysis conditions,
   configured to subtract all executed combinations of the values of the control parameters corresponding to the plurality of analysis conditions stored in the memory, from the all combinations of the values of the control parameters, so as to extract all unexecuted combinations of the values of the control parameters, and
   configured to create a list of unexamined analysis conditions including the all unexecuted combinations of the values of the control parameters;
   c) a method file creator configured to create one or more of method files corresponding to one or more of the analysis conditions included in the list; and
   d) a display section configured to display the list.

2. The chromatograph data processing system according to claim 1, wherein
   the unexamined analysis condition creator further acquires chromatograms respectively obtained for the plurality of analysis conditions under which the analyses have been executed, and
   the chromatograph data processing system displays one or more of the chromatograms on the display section.

3. A chromatograph data processing method used for a chromatograph comprising the steps of:
   a) storing, into a memory, a plurality of analysis conditions under which analyses have been executed for a sample, the plurality of analysis conditions being described in a schedule table, each of the plurality of analysis conditions being defined by a combination of values of control parameters;
   b) creating all combinations of the values of the control parameters included in all of the plurality of analysis conditions;
   c) subtracting all executed combinations of the values of the control parameters corresponding to the plurality of analysis conditions stored in the memory, from the all combinations of the values of the control parameters, so as to extract all unexecuted combinations of the values of the control parameters;
   d) creating a list of unexamined analysis conditions including the all unexecuted combinations of the values of the control parameters;
   e) creating one or more of method files corresponding to one or more of the analysis conditions included in the list; and
   f) displaying the list on a display section.

4. The chromatograph data processing method according to claim 3, further comprising a step of acquiring chromatograms respectively obtained for the plurality of analysis conditions under which the analyses have been executed and displaying one or more of the chromatograms.

* * * * *